United States Patent [19]

Fogg et al.

[11] 4,209,802
[45] Jun. 24, 1980

[54] GLASS FRAGMENT DETECTOR

[75] Inventors: Daniel A. Fogg, Bradenton, Fla.; Maurice W. Brandt; Marshall Klemundt, both of Freemont, Mich.

[73] Assignee: Gerber Products Company, Fremont, Mich.

[21] Appl. No.: 939,530

[22] Filed: Sep. 25, 1978

[51] Int. Cl.² ............................................. H04N 7/18
[52] U.S. Cl. ................................. 358/106; 209/939; 250/223 B; 356/240; 356/427
[58] Field of Search ........ 358/106; 356/240, 426–428; 250/223 B; 209/939

[56] References Cited

U.S. PATENT DOCUMENTS

| 1,383,739 | 7/1921 | Meyer | 356/240 |
|---|---|---|---|
| 2,021,696 | 11/1935 | Miller | 356/240 |
| 2,196,389 | 4/1940 | Fogg | 356/240 |
| 3,180,994 | 4/1965 | Rottmann | 356/428 |
| 3,479,514 | 11/1969 | Kidwell | 250/223 B |
| 3,765,533 | 10/1973 | Stephens | 209/939 |
| 3,778,617 | 12/1973 | Calhoun | 250/223 B |
| 3,827,812 | 8/1974 | Heimann | 250/223 B |
| 3,918,570 | 11/1975 | Dunham | 250/223 B |
| 3,932,042 | 1/1976 | Faani | 356/240 |
| 3,958,078 | 5/1976 | Fowler | 358/106 |
| 4,108,762 | 8/1978 | Babunovic | 250/223 B |
| 4,136,930 | 1/1979 | Gomm | 358/106 |

Primary Examiner—Howard W. Britton

[57] ABSTRACT

Apparatus and method for detecting glass fragments within closed filled jars on a production line. A plurality of jars is conveyed in serial fashion past an inspection station. Prior to arrival at the inspection station the jars are tilted by an acute angle of approximately 45° to define a lowermost portion of the jar bottom into which glass fragments and the like settle. A light source illuminates this lowermost portion at the inspection station, and a television camera is precisely focused on the lowermost portion. The camera relays a signal for producing a magnified image on a monitor so that an operator can divert jars containing foreign matter out of the line.

11 Claims, 5 Drawing Figures

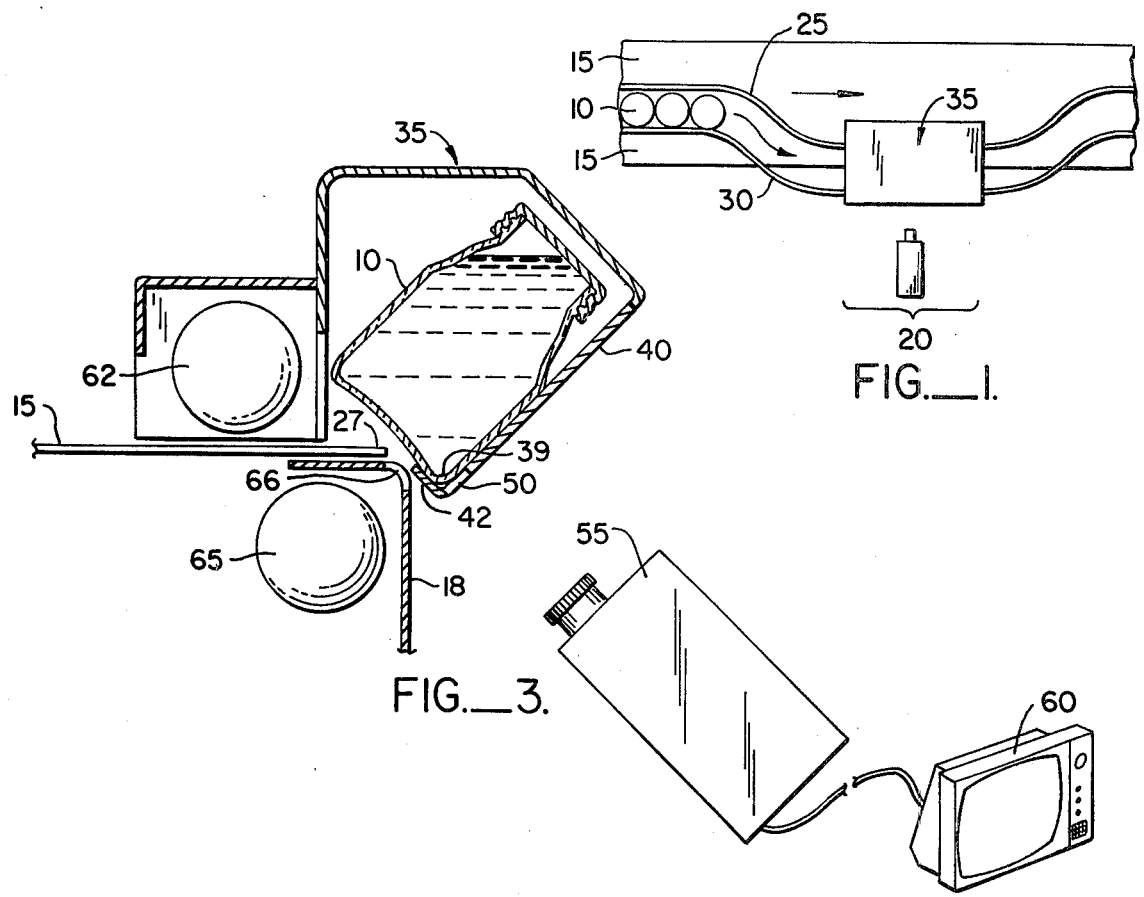
FIG._1.
FIG._3.
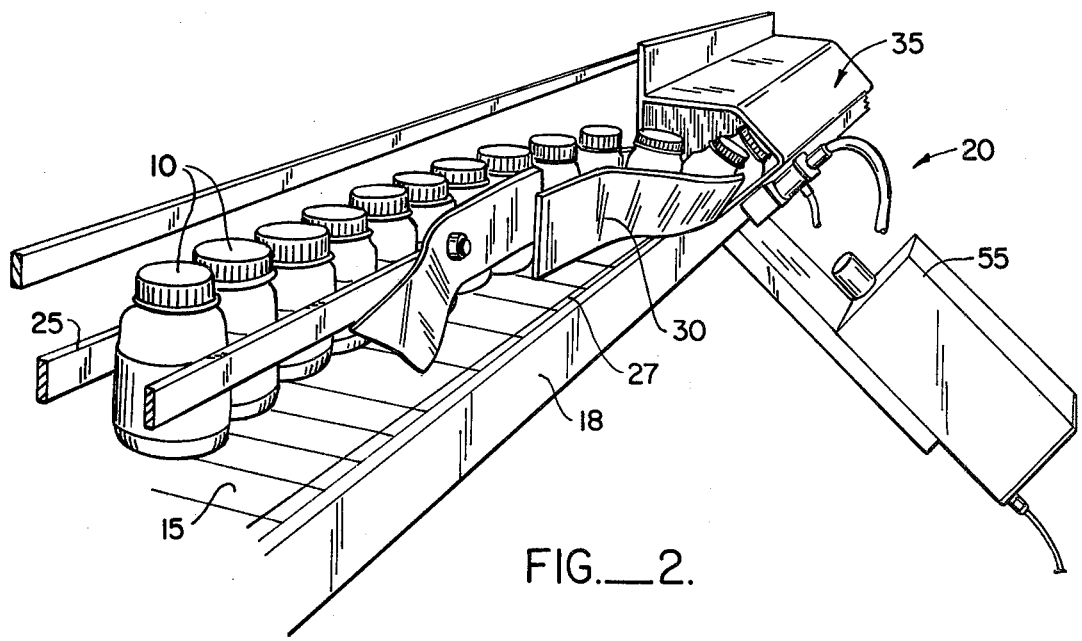
FIG._2.

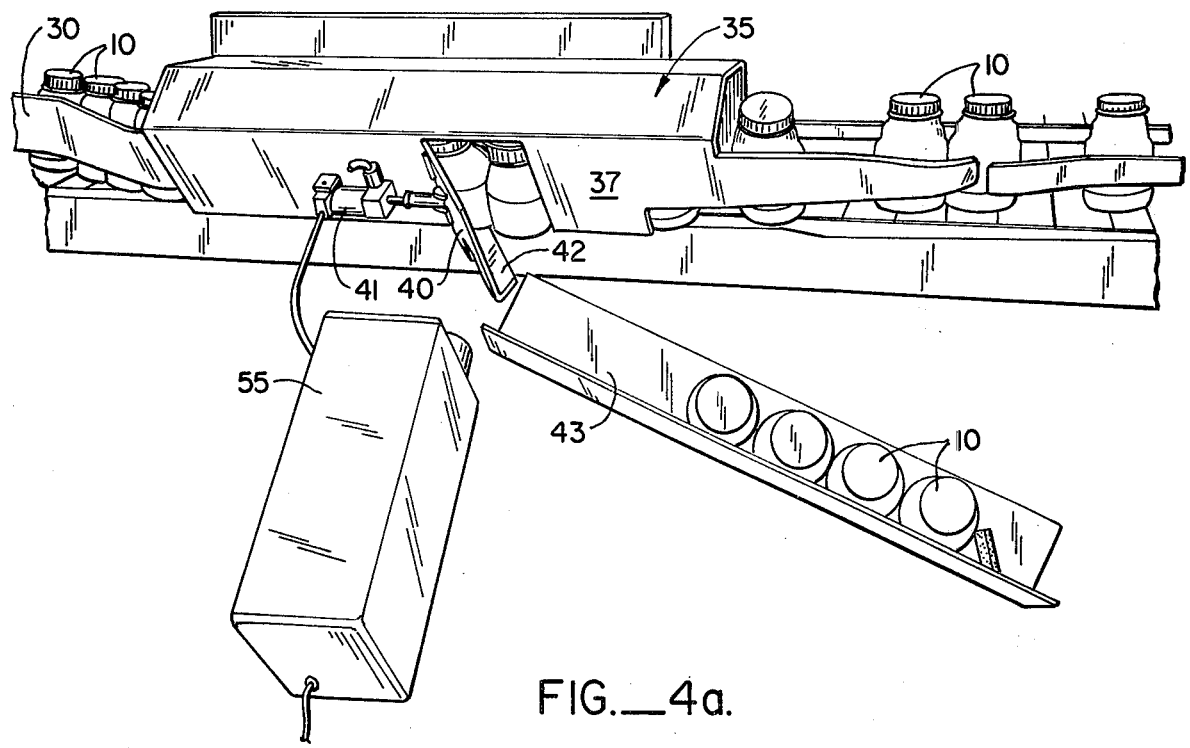
FIG.—4a.
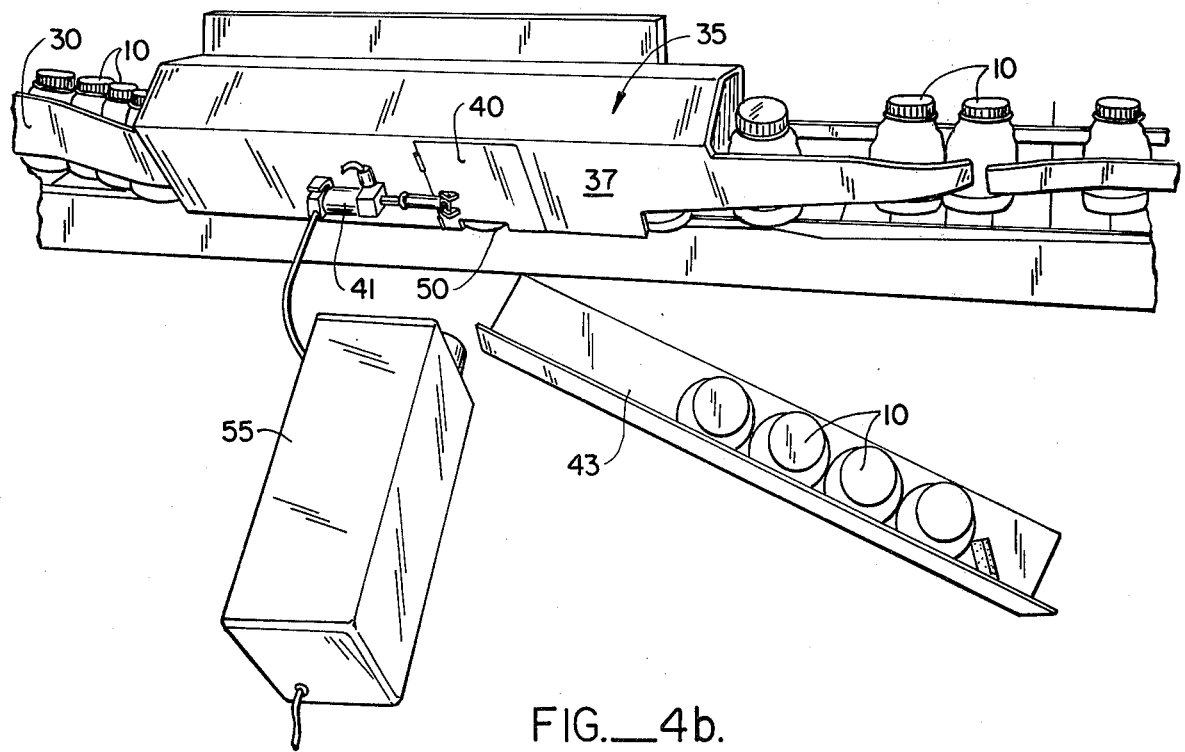
FIG.—4b.

GLASS FRAGMENT DETECTOR

BACKGROUND OF THE INVENTION

This invention relates to a system for discerning foreign objects not readily discernible to the eye, such as minute glass particles, in the bottom of glass jars, particularly the type of jar whose internal bottom surface is characterized by a peripheral concave region and a central convex hump.

During the packaging of food in glass jars on a production line, the jars are subjected to a number of operations, any of which has the potential of causing breakage. Typically, the jars are inverted and washed, filled, capped, and labelled prior to packing in cases. It will be noted that a number of these operations occur during the time that the jars adjacent to a jar that is broken are open. Thus, there is the danger that glass fragments from the broken jar will find their way into the adjacent jars. Ingestion of food containing such glass fragments, especially by an infant, has potentially catastrophic consequences, and must be scrupulously avoided.

When a broken jar is detected, it is sound procedure to stop the production line and inspect a number of jars that passed through the line on either side of the broken jar. At least several hundred jars on either side of the broken jar are typically inspected. Additionally, even if the broken jar itself is not detected at the time of breakage, standard quality control checks for broken glass are made at frequent intervals and the line can be stopped in order to inspect jars that have been handled during the immediately preceding interval.

Several schemes for inspecting jars on a production line basis are known. However, most of these prior art methods relate to the inspection of empty jars with open mouths. Such prior art methods are wholly unsuitable for inspecting closed jars containing food. Yet, it is closed, full jars that need to be inspected when a broken jar is discovered at some point on the production line.

Many of the prior art methods of inspecting jars require that the jar be rotated during inspection in order to render visible foreign material in the bottom. This is especially true where the inner surface of the jar bottom has a central convex hump. Such rotation of the jar necessitates additional handling and registration which slow down the process, making it difficult to inspect a large number of jars in a reasonable time. Moreover, the additional handling itself increases the chance of further breakage.

SUMMARY OF THE INVENTION

The present invention provides apparatus for and a method of discovering glass fragments and other foreign matter in closed jars containing translucent food. Broadly, jars to be inspected are passed along a conveyor to an inspection station. Prior to arrival at the inspection station the jars are tilted to one side at an acute angle, thereby defining a lowermost portion of the contents in contact with the jar bottom. A 45° angle has been found to be suitable. Glass fragments or other foreign matter settle to the lowermost portion. As it passes the inspection station, the tilted jar is illuminated from the other side and the lowermost region of the jar is viewed by a television camera. The television camera is preferably tilted at a corresponding angle so that it is directed generally perpendicular to the jar side in the tilted condition. The television camera produces an image of the lowermost region of the jar which can be viewed in magnified form on a monitor. An operator stationed at the monitor views the jars, which may pass by the inspection station at a rate of approximately 60 jars per minute.

Since the present invention provides for inspection of closed, full jars, it makes possible the detection of glass fragments arising from breakage during the filling and capping operations. Additionally, foreign matter from the actual contents introduced into the jars can be detected.

The tilting of the jars and subsequent inspection in the single tilted position has the advantage that the foreign material is localized in a small region, thereby allowing quicker viewing since it is not necessary to rotate the jar. Tilting the jar also has the advantage that multiple fragments, perhaps too small to be seen or detected individually, are concentrated within a limited space and in the aggregate rendered more visible.

Additionally, the localization allows very precise focusing of the television camera, thereby rendering the procedure highly sensitive. In particular, the television camera may be positioned quite close to the jar while maintaining any foreign material within the limited depth of field available at such close distances. This results in a magnified image of high resolution which allows the operator to detect fragments as small as 0.5 mm in diameter.

The present invention is suitable for inspecting jars containing any translucent material of low viscosity. The contents of the jar need not be transparent since the fragments to be detected are immediately adjacent an inner surface of the jar. The requirement that the contents be translucent arises from the need to illuminate the jar from the opposite side to that on which the television camera is located.

BRIEF DESCRIPTION OF THE DRAWINGS

FIG. 1 is a schematic plan view of a plurality of jars on a production line undergoing inspection according to the present invention;

FIG. 2 is a perspective view of a plurality of jars on a production line undergoing inspection according to the present invention;

FIG. 3 is a sectional view of a jar undergoing inspection according to the present invention;

FIG. 4a is a top perspective view illustrating a mechanism wherein defective jars are diverted from the production line; and FIG. 4b is a view similar to FIG. 4a, illustrating the apparatus in a condition when it is not desired to reject the jar.

DESCRIPTION OF THE PREFERRED EMBODIMENT

Referring first to FIGS. 1 and 2, a plurality of jars 10 is carried on a conveyor past an inspection station 20. The conveyor typically includes a conveyor belt 15 and side rail supports 18. Jars 10 have typically already been filled with a translucent, fluid substance, and capped. Prior to arrival at inspection station 20, jars 10 are generally moving along the direction of conveyor belt 15 in an upright position. A deflection rail 25 deflects jars 10 transversely to an edge 27 of conveyor 15 prior to their arrival at inspection station 20 such that about half the jar bottom extends over the edge. A slanted fence 30, prevents the jars from falling over, and guides the jars into a housing 35 of inspection station 20.

Referring now to FIGS. 2, 3, 4a, and 4b, the configuration of inspection station 20 may be seen. Housing 35 has an inclined wall 37 against which the jars lean at an acute angle from the vertical. An angle of approximately 45° has been found to be suitable. This tilt defines a lowermost portion 39 of the internal surface of jar 10. A portion 40 of wall 37 is cut out and hingedly fastened to the remaining portions of wall 37 to define a generally downwardly and outwardly opening door. The opening of this door may be controlled by an actuator 41 which may be a solenoid or a pneumatic device. A hopper 43 is disposed proximate door 40 to receive jars when door 40 is opened. Wall 37 including door portion 40 include a lower flange 42 for supporting lowermost portion 39 of a jar 10 within housing 35. FIG. 4a shows door 40 in an opened position, such that jars passing thereby roll downwardly along flange 42 into hopper 43. Jars moving through housing 35 do not contact conveyor 25, but rather are supported in the trough defined by wall 37 and flange 42. The jars that are still on conveyor 25 (not having arrived at inspection station 20) push the jars ahead of them to move them through the inspection station. Friction between the jars tends to result in a sliding rather than a rolling motion. A portion of door 40 proximate flange 42 is cut away to define a horizontally extending slit 50 generally opposite lowermost portion 39 of jar 10.

A television camera 55 is situated opposite slot 50 with its axis directed perpendicularly to door 40 and pointed at slot 50. Thus television camera 55 views lowermost portion 39 of jar 10 as it passes slot 50. Associated with camera 55 is necessary circuitry for producing a signal to form an image on a television monitor 60, for viewing by an operator stationed at the monitor. Alternate means of viewing the lowermost portion 39 of the tilted jar 10, such as a combination of lenses focusing on such portion 39 which produces a magnified image, may be used in lieu of the television camera 55.

Means is provided for illuminating those portions of the contents of jar 10 in the vicinity of lowermost portion 39. A first light bulb 62 is mounted to the side of housing 35 remote from wall 37 to illuminate jar 10 from the side remote from camera 55. A second light bulb 65 is mounted under conveyor belt 15 to illuminate jar 10 from beneath. Support rail 18 is provided with an aperture 66 to permit such illumination.

Having discussed the apparatus of the present invention, the operation can now be understood.

As jars 10 move into housing 35 in their tilted condition, any glass fragments or other foreign material within the jars gravitate toward lowermost portion 39. In order that small particles gravitate toward the bottom, the contents of jars 10 must be sufficiently fluid to allow such settling. As a practical matter, for particles of the order of 1 millimeter in diameter, the contents must be liquid. Any vibration of the jars tends to promote the settling and localization of foreign material in the jars. A separate vibrator is not necessary since the jars undergo vibration in their travel through the inspection station. As the jars pass slot 50, television camera 55 produces and relays an image of lowermost portion 39 to an operator viewing monitor 60. In order that foreign objects be illuminated by light bulbs 62 and 65, the contents of jar 10 must be translucent. It is not necessary that they be transparent, since the foreign matter settles to a region immediately adjacent the wall of jar 10.

The localization of foreign matter at lowermost portion 39 has the desirable consequence that multiple particles, perhaps too small to be individually seen, come together in a small region thereby rendering them visible in the aggregate. Since the particles congregate in a small region, camera 55 may be positioned quite close to slot 50 while maintaining all such particles in precise focus. This may be especially significant in low light situations where depth of field is limited.

The result is a greatly magnified image of high resolution on monitor 60, which allows the operator to detect particles as small as 0.5 mm in diameter. The operator, upon seeing a jar containing a foreign particle, activates actuator 41 to open door 40, thereby allowing the suspect jar to drop into hopper 43, thus removing it from the production line.

We claim:

1. Apparatus for aiding an operator in the visual inspection of jars filled with translucent material comprising:
    means for tilting the jars by an angle less than 90°, thereby defining a lowermost portion of the jar bottom, such that solid material within the jar gravitates to and is localized at the lowermost portion;
    means for transporting the jars in their tilted position along a predetermined path past an inspection station;
    means for forming a magnified visual image, such means situated sufficiently close to lowermost portion to precisely focus on said portion while producing a clear, sharp magnified image of high resolution.

2. The invention of claim 1 wherein the image forming means comprises:
    means for illuminating the lowermost portion of the jar bottoms;
    a television camera directed at the lowermost portion of the tilted jars; and
    a television monitor coupled to the television camera to provide a magnified image of the lowermost portion of the jar bottom for the operator.

3. Apparatus for facilitating the detection by an operator of solid material in a plurality of liquid-filled jars comprising:
    means for tilting the jars to define a lowermost portion of the interior of the jar, so that solid matter within the jar settles to and is localized at the lowermost portion of the jar interior;
    means for moving the jars in serial fashion along a predetermined path past an inspection station;
    means for illuminating the lowermost region of the jar;
    a television camera directed at the lowermost portion of the tilted jars; and
    a television monitor coupled to the television camera to provide a magnified image of the lowermost portion of the jar bottom for the operator.

4. Apparatus for facilitating the detection by an operator of solid material in a plurality of jars filled with translucent liquid contents comprising:
    a conveyor for carrying the jars along a predetermined path for deflecting the jars at least partially over an edge of the conveyor;
    a slanted fence for preventing the jars from falling off the edge of the conveyor; a housing at the inspection station for receiving the jars, the housing including a slanted wall and a flange which together form a trough for supporting the jars at an acute angle from the vertical, thereby defining a lowermost portion of the jar contents such that solid material in the jar settles to and is localized at the lowermost portion opposite the slit;

the slanted wall and flange having portions defining a slit opposite the lowermost portion of a jar passing through the housing;

a light source for illuminating a region of the jar contents including the lowermost portion;

a television camera directed at the slit; and a television monitor coupled to the television camera;

such that the localization of the solid material allows the television camera to be located at a sufficiently small distance from the slit to produce a magnified image of high resolution, thereby allowing the detection of particles too small to be readily discernible to the eye.

5. The invention of claim 4 wherein the acute angle is approximately 45°.

6. The invention of claim 4 wherein the television camera is oriented perpendicular to the slanted wall.

7. The invention of claim 4 wherein the slanted wall includes a door for allowing a jar to be selectively removed from the housing.

8. A method of visually detecting solid material within a liquid-filled jar comprising the steps of:
    tilting the jar, thereby defining a lowermost portion of the jar, such that solid material in the jar settles to and is localized at the lowermost portion;
    moving the tilted jar along a predetermined path past an inspection station;
    positioning an image capture means near said lowermost portion;
    focusing said image capture means on said lowermost portion; and
    producing a clearly defined magnified image of the lowermost portion of the jar for inspection by an operator, whereby the visibility of the solid material is enhanced.

9. A method in accordance with claim 8 and further characterized by the step of illuminating the lowermost portion of the jar at least while the magnified image is being produced.

10. A method in accordance with claim 8 wherein said jars are tilted approximately 45°.

* * * * *